US009278033B2

(12) United States Patent
Abraham et al.

(10) Patent No.: US 9,278,033 B2
(45) Date of Patent: Mar. 8, 2016

(54) CONTACTLESS PASSIVE SENSING FOR ABSORBENT ARTICLES

(75) Inventors: Jose Kollakompil Abraham, Neenah, WI (US); Joseph Raymond Feldkamp, Appleton, WI (US); Shawn Jeffery Sullivan, Neenah, WI (US); Sridhar Ranganathan, Suwanee, GA (US); Aster Ellen Kammrath, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1112 days.

(21) Appl. No.: 13/302,185

(22) Filed: Nov. 22, 2011

(65) Prior Publication Data

US 2013/0131618 A1    May 23, 2013

(51) Int. Cl.
*A61F 13/42* (2006.01)

(52) U.S. Cl.
CPC ...................................... *A61F 13/42* (2013.01)

(58) Field of Classification Search
CPC ........................... A61F 13/42; A61F 2013/424
USPC ......................................................... 604/361
See application file for complete search history.

(56) References Cited

U.S. PATENT DOCUMENTS

| | | | |
|---|---|---|---|
| 4,399,404 A | 8/1983 | Resh | |
| 4,653,491 A | 3/1987 | Okada et al. | |
| 5,463,377 A | 10/1995 | Kronberg | |
| 5,903,222 A | 5/1999 | Kawarizadeh et al. | |
| 5,904,671 A | 5/1999 | Navot et al. | |
| 6,112,580 A * | 9/2000 | Hesky | 73/49.1 |
| 6,206,835 B1 | 3/2001 | Spillman, Jr. et al. | |
| 6,373,395 B1 | 4/2002 | Kimsey | |
| 6,583,722 B2 | 6/2003 | Jeutter et al. | |
| 6,774,800 B2 | 8/2004 | Friedman et al. | |
| 7,394,391 B2 * | 7/2008 | Long | 340/573.5 |
| 7,489,252 B2 | 2/2009 | Long et al. | |
| 7,600,423 B1 * | 10/2009 | Fluhler | G01F 23/26 73/290 B |

(Continued)

FOREIGN PATENT DOCUMENTS

| | | |
|---|---|---|
| DE | 3437950 A * | 4/1985 |
| JP | 2007-143994 A | 6/2007 |

(Continued)

OTHER PUBLICATIONS

Bakhoum, et al. "Miniature moisture sensor based on ultracapacitor technology", IEEE Transactions on Components, Packaging and Manufacturing Technology, vol. 2, No. 7, Jul. 2012.*

(Continued)

*Primary Examiner* — Susan Su
(74) *Attorney, Agent, or Firm* — Kimberly-Clark Worldwide, Inc.

(57) ABSTRACT

An absorbent article facilitating sensing the presence of a body exudate in the absorbent article includes an absorbent member; a sensor coil disposed on or in the article; and an electrical double-layer capacitor disposed on or in the article and in electrical communication with the sensor coil, wherein the capacitor is in fluid communication with the absorbent member. An absorbent article system also includes a detector circuit including an exciter coil configured for electromagnetic communication with the sensor coil, and sensor electronics configured to indicate the presence of a body exudate based on changes in the electromagnetic communication between the exciter coil and the sensor coil.

20 Claims, 6 Drawing Sheets

(56) References Cited

U.S. PATENT DOCUMENTS

| | | | |
|---|---|---|---|
| 7,642,396 B2 | 1/2010 | Ales et al. | |
| 7,700,821 B2 | 4/2010 | Ales et al. | |
| 2001/0051766 A1* | 12/2001 | Gazdzinski | 600/309 |
| 2002/0049389 A1* | 4/2002 | Abreu | A61B 3/1241 600/558 |
| 2002/0070864 A1 | 6/2002 | Jeutter et al. | |
| 2002/0070868 A1 | 6/2002 | Jeutter et al. | |
| 2003/0060789 A1 | 3/2003 | Shapira et al. | |
| 2003/0214399 A1* | 11/2003 | Naruse et al. | 340/531 |
| 2004/0064114 A1 | 4/2004 | David et al. | |
| 2004/0078014 A1 | 4/2004 | Shapira | |
| 2005/0079781 A1* | 4/2005 | Tsujimoto et al. | 442/59 |
| 2008/0033383 A1 | 2/2008 | Cantor et al. | |
| 2008/0051745 A1 | 2/2008 | Long et al. | |
| 2008/0074274 A1 | 3/2008 | Hu et al. | |
| 2008/0147031 A1 | 6/2008 | Long et al. | |
| 2008/0278337 A1 | 11/2008 | Huang et al. | |
| 2008/0300559 A1* | 12/2008 | Gustafson | A61F 13/42 604/361 |
| 2009/0036850 A1* | 2/2009 | Nhan et al. | 604/361 |
| 2009/0124990 A1 | 5/2009 | Feldkamp et al. | |
| 2009/0201142 A1 | 8/2009 | Zou et al. | |
| 2009/0326417 A1 | 12/2009 | Ales et al. | |
| 2010/0152688 A1* | 6/2010 | Handwerker et al. | 604/361 |
| 2010/0164733 A1 | 7/2010 | Ales et al. | |
| 2010/0168702 A1 | 7/2010 | Ales et al. | |
| 2010/0219841 A1 | 9/2010 | Feldkamp et al. | |
| 2011/0130813 A1* | 6/2011 | Moreshead | A61F 13/00051 607/112 |
| 2012/0165772 A1* | 6/2012 | Groosman | A61F 13/42 604/361 |
| 2013/0041334 A1* | 2/2013 | Prioleau | A61F 13/42 604/361 |
| 2014/0296808 A1* | 10/2014 | Curran et al. | 604/361 |

FOREIGN PATENT DOCUMENTS

| | | |
|---|---|---|
| WO | WO 99/33037 A1 | 7/1999 |
| WO | WO 02/052302 A2 | 7/2002 |
| WO | WO 2010/012217 A1 | 2/2010 |
| WO | WO 2010/049829 A2 | 5/2010 |
| WO | WO 2010/123425 A1 | 10/2010 |

OTHER PUBLICATIONS

Sierociuk, et al. "Resonance phenomena in circuits with ultracapacitors".*

* cited by examiner

CONTACTLESS PASSIVE SENSING FOR ABSORBENT ARTICLES

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. Many absorbent articles, especially those sold under the trade name HUGGIES™ by the Kimberly-Clark Corporation, are so efficient at absorbing liquids that it is sometimes difficult to tell whether or not the absorbent article has been insulted with a body exudate, especially when the absorbent article is being worn by a newborn or other very young wearers. Insult amounts in such wearers tend to be very small. Other wearers might also produce very small insults.

Accordingly, various types of moisture or wetness indicators have been suggested for use in absorbent articles. The wetness indicators include various passive indicators such as indicator strips, printing, or other devices within each absorbent article. Wetness indicators can also include alarm devices that are designed to assist parents or attendants in identifying a wet diaper condition early on. These devices produce either a visual or an audible signal.

Electronic insult/status detection in absorbent articles mainly depends on resistive, capacitive, inductive or optical sensors that are placed at the insult locations. All these sensors require either an electronic circuit that has to be directly in contact with the sensing electrodes, or conventional sensor components of limited effectiveness and range. These sensing electrodes placed at the insult locations can monitor the insult by measuring any changes in its resistance, capacitance or impedance characteristics. This makes it difficult to monitor the wetness/status of articles that are in intimate contact with the human body such as feminine hygiene products. Tampon users are often concerned with the status of the article. An efficient technology to monitor the status, fullness, and/or time-to-change status is still an unmet challenge.

Problems, however, have been encountered in designing a signaling device that can be used as desired but that does not appreciably increase the cost of each absorbent article, while providing a meaningful signal to the caregiver.

SUMMARY

The present inventors undertook intensive research and development efforts with respect to improving absorbent articles, particularly in providing a wetness indicator, a need that exists for wetness detection in diapers, feminine products, and incontinence products. Technology that can be implemented without altering absorbent article construction is preferred. A non-contact and passive technology has been developed to monitor the status of the absorbent article. The sensor status can be read using an electronic circuit external to the article.

A noninvasive induction type sensor measures electrical conductivity at some depth within an absorbent article. A useful approach is an induction coil conductivity sensor, which can be attached to an appropriate target zone on or in the absorbent article. The induction coil, forming part of a resonant circuit, experiences an impedance change when conductive liquid is placed nearby. This impedance change is detected in a marginal oscillator circuit, with its output interpreted to reflect a wetness level.

The present application describes an absorbent article facilitating sensing the presence of a body exudate in the absorbent article, the article including an absorbent member; a sensor coil disposed on or in the article; and an electrical double-layer capacitor disposed on or in the article and in electrical communication with the sensor coil, wherein the capacitor is in fluid communication with the absorbent member.

The present application also describes an absorbent article system for sensing and indicating the presence of a body exudate in an absorbent article, the system including an absorbent article including an absorbent member, a sensor coil disposed on or in the article, and an electrical double-layer capacitor disposed on or in the article and in electrical communication with the sensor coil, wherein the capacitor is in fluid communication with the absorbent member. The system also includes a detector circuit including an exciter coil configured for electromagnetic communication with the sensor coil, and sensor electronics configured to indicate the presence of a body exudate based on changes in the electromagnetic communication between the exciter coil and the sensor coil.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

FIG. 4(*b*) illustrates the change in sensor output in volts as a function of time following an insult to a tampon of FIG. 3;

Figure 1:
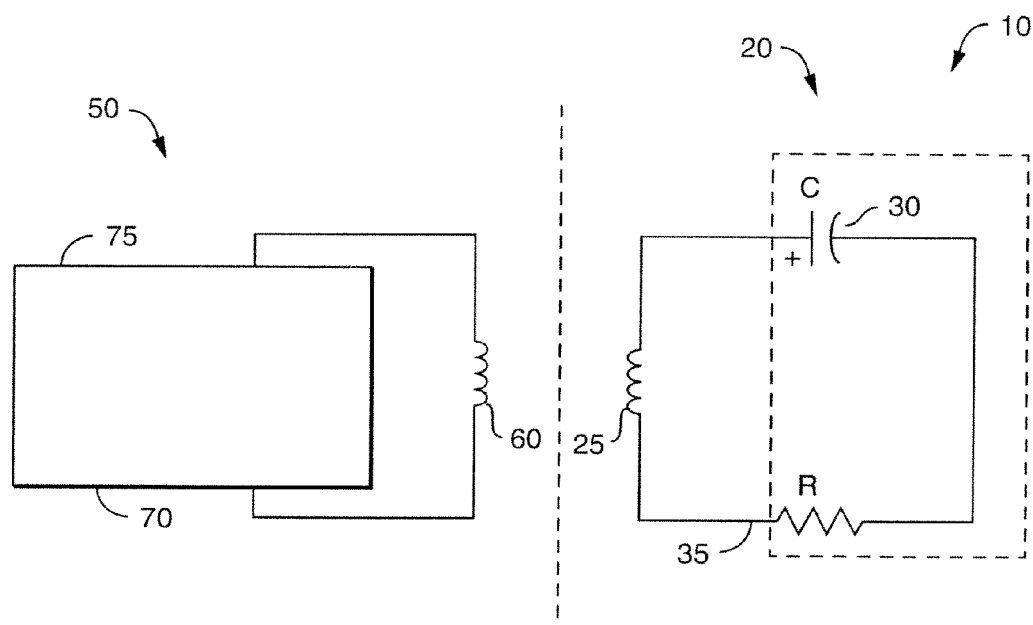
FIG. 1 is a schematic of the wetness sensor system of the present application.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

The present disclosure is generally directed to absorbent articles adapted to indicate the presence of a body exudate in the absorbent article or other changes in the condition of the product or wearer. The absorbent article can be, for instance, a diaper, a training pant, an incontinence product, a feminine hygiene product, a medical garment, a bandage, or the like. Generally, the absorbent articles are disposable, meaning that they are designed to be discarded after a limited use rather than being laundered or otherwise restored for reuse.

Described herein is a non-contact electronic sensing/monitoring device employing a technology based on remote query inductive coupling to an electrical double-layer capacitor sensor on or in an absorbent article 100. The double-layer capacitive sensor receives excitation remotely.

As shown in FIG. 1, the wetness detection system 10 of the present application includes article-based components 20 and off-article components or detector circuit 50. The article-based components 20 include a sensor coil 25 and an electrical double-layer capacitor 30, and the off-article components 50 include an exciter coil 60 and sensor electronics 70. It should be noted that the wetness detection system 10 can also be configured as an article fullness or leakage warning system as described in more detail below.

The article-based components 20 of the wetness detection system 10 include a sensor coil 25 disposed on or in the disposable absorbent article 100. The sensor coil 25 is a passive induction coil that receives energy from outside the disposable absorbent article 100. In general, the response of the sensor coil 25 to an outside energy source differs depending on the presence and amount of body exudates in the absorbent article 100.

The sensor coil 25 can be primarily metallic wire or other metallic form, a conductive woven or nonwoven including conductive paper, an RFID tag, printed conductive ink, or otherwise deposited on or in the disposable absorbent article 100. See U.S. patent application Ser. No. 12/971,741 for additional detail related to conductive nonwovens. The sensor coil 25 can be disposed on or in the disposable absorbent article 100 in any suitable location including in a urine target zone, a fecal target zone, or adjacent an edge of the disposable absorbent article 100 to allow for a leakage warning to the wearer or caregiver. In addition, the disposable absorbent article 100 can include two or more sensor coils 25 to either sense wetness in more than one location, or to estimate the level of fullness of the disposable absorbent article 100. Additional details and use of the sensor coil 25 are described below.

With respect to specific sensor coil locations, the sensor coil 25 can be disposed on an outer surface of the disposable absorbent article 100. In this aspect, the sensor coil 25 is in electromagnetic communication with the absorbent core of the disposable absorbent article 100, but not necessarily in fluid communication with the absorbent core. For disposable absorbent articles 100 that include an outer cover or cover sheet 105, 205, the sensor coil 25 can be disposed on an inner surface of the outer cover or cover sheet 105, 205, or on an outer surface of the outer cover or cover sheet 105, 205. The sensor coil 25 can be disposed an virtually any surface, internally or externally, of the disposable absorbent article 100, although the sensor coil 25 is, for example, preferably not disposed on a skin-contacting surface if the sensor coil 25 includes metallic wire. The sensor coil 25 can, for example, be printed on a skin-contacting surface of the disposable absorbent article 100. The sensor coil 25 is preferably disposed on the inside surface of the outer cover or cover sheet 105, 205.

In one aspect of the present disclosure illustrated in FIG. 1, the wetness detection system 10 includes a sensor circuit 35 that is adapted to detect the presence of a body exudate in the absorbent article 100. The sensor circuit 35 includes a sensor coil 25 that, when placed in the vicinity of a conductive liquid such as urine and energized by the exciter coil 60, will generate weak electrical eddy currents in the liquid. The electrical currents in turn generate a field that couples with the sensor coil 25 and changes its impedance—both real and imaginary parts. The sensor coil 25 can be separately attached to or within the disposable absorbent article 100 or it can be part of the disposable absorbent article 100 (e.g., it can be the string of a tampon).

Sensor coils 25 can be made as small as having a diameter of about 1.0 mm, although the field of view of the sensor coil 25 is reduced as the size of the sensor coil 25 is reduced. Sensor coils 25 can also be made large to increase the field of view, with diameters as large as 10 cm, but larger sensor coils 25 can become impractical for use with absorbent article applications. Although sensor coils 25 of any size can be used, sensor coils 25 in the range of about 0.5 cm to about 8 cm are more practical. Likewise, sensor coils 25 in the range of about 1 cm to about 5 cm have additional advantages. Finally, sensor coils 25 in the range of about 1 cm to about 2 cm have the most practicality. The sensor and exciter coils 25, 60 can be of any suitable shape required by the product specification.

The electronics associated with the sensor circuit 35 are relatively simple and can be miniaturized to postage stamp size. The sensor circuit 35 includes the sensor coil 25, which in one example includes about 40 turns of #36 wire formed into a planar loop about 2 cm in diameter.

The sensor circuit 35 within or on the absorbent article 100 further includes an electrical double-layer capacitor 30. The electrical double-layer capacitor 30 is disposed on or in the absorbent article 100 and is in electrical communication with the sensor coil 25. The electrical double-layer capacitor 30 is also in fluid communication with the absorbent core of the absorbent article 100. The electrical double-layer capacitor 30 includes a pair of plates each having a proximal end adjacent the sensor coil 25 and a distal end spaced apart from the sensor coil 25. The plates can be rectilinear, tapered, or of any other suitable shape. In one aspect of the present application, the plates taper in width from the proximal end to the distal end.

Tapered plates or electrodes allow the sensitivity of detection to become enhanced as the insult volume grows. Whereas sensitivity becomes limited without such geometry, sensitivity is improved for later stages of insult because the area of the electrodes in contact with the insult liquid grows more rapidly with insult volume than it would with rectangular electrodes. The capacitance of a parallel plate capacitor is proportional to the area of the plates and the dielectric properties of the medium in between the plates. Theoretical calculations prove that the change in capacitance in a rectangular plate capacitor is linearly proportional to the area. The tapered parallel plate capacitor design adopted here has the advantage over the conventional rectangular design in that the change in capacitance is exponentially proportional to the area. This yields greater sensitivity for sensing in absorbent articles.

Various other shapes such as a comb shape, a triangular shape, etc. and modifications to the present design can be practiced by those of ordinary skill in the art to provide an electrical double-layer capacitor 30.

The plates of the electrical double-layer capacitor 30 can be manufactured from any suitable material, but are preferably manufactured from a carbon-based conductive web for at least the reasons of recyclability and the avoidance of metallic elements within the absorbent article 100. In one aspect, the electrical double-layer capacitor 30 incorporates conductive paper of the types described in U.S. Patent Application Publication No. 2009/0321238 and entitled "Conductive Webs Containing Electrical Pathways and Method for Making Same." In another aspect, the electrical double-layer capacitor 30 can be printed on an outer surface of the absorbent article 100, or on the inner surface of the outer cover 105 of the absorbent article 100 (e.g., using flexographic printing of conductive ink). In yet another aspect, the electrical double-layer capacitor 30 can be manufactured separately from much of the absorbent article 100 and then inserted into the absorbent article 100.

Unlike previous wetness sensing methods, the technique described herein does not measure resistance between electrodes. Rather, a falling resistance between the electrodes upon insult allows the electrode/electrolyte system to function as a capacitor with capacitance increasing as the intervening resistance falls. A key distinction of the present application is that electrode voltages are so low (<10 mv) that electrochemical action at the electrodes does not happen. As a result, the electrode/electrolyte system does not function as a resistor, but rather as a capacitor whose capacitance is tuned by the intervening electrolyte. In other words, the intrusion of electrolyte into the intervening space between electrodes activates the capacitor, allowing it to register a capacitance that grows with increasing amounts of electrolyte.

The sensor circuit 35 can assist in identifying the position of and discriminate the insult by measuring the capacitance change. More accurate and efficient position and location data, if desired, can be achieved using time domain reflectrometric techniques.

Excitation voltages applied to the electrical double-layer capacitor are relatively small. Excitation voltages are less than 100 mv, and preferably less than 50 mv, and more preferably less than 10 mv. In general, if excitation voltages are too high, the capacitance function can be lost.

In addition to electrode geometry, the sensitivity of the circuit is also influenced by the surface area of the conductive fibers embedded in the conductive web used to make the electrodes in some aspects. In the construction of the conductive web, both high surface area fibers and a large number of such fibers per unit volume are preferred. The conductive web includes conductive fibers with a total surface area of at least 5 square meters per gram of web material, and preferably of at least 50 square meters per gram of web material, and more preferably of at least 100 square meters per gram of web material, and still more preferably of at least 400 square meters per gram of web material. Unlike conventional capacitors that need to have their electrodes very close together, the electrodes of electrical double-layer capacitors can be far apart and still work quite well.

The electrical double-layer capacitor 30, also known as a supercapacitor or an ultracapacitor, differs from a regular capacitor in that it has a very high capacitance. A capacitor stores energy by means of a static charge as opposed to an electrochemical reaction. The modern electrical double-layer capacitor employs battery technology by using special electrodes and electrolyte. The electrical double-layer capacitor 30 is carbon-based and has an organic electrolyte. Additional information can be found, for example, at: www.electrochemsci.org/papers/vol3/3111196.pdf.

In another aspect of the present disclosure (not shown), the sensing circuit 35 uses more than one sensor coil 25. For example, two sensor coils 25 can be positioned such that one is near the front of the absorbent article 100 to detect urine and the other is near the rear of the absorbent article 100 to detect fecal matter.

Figure 2:
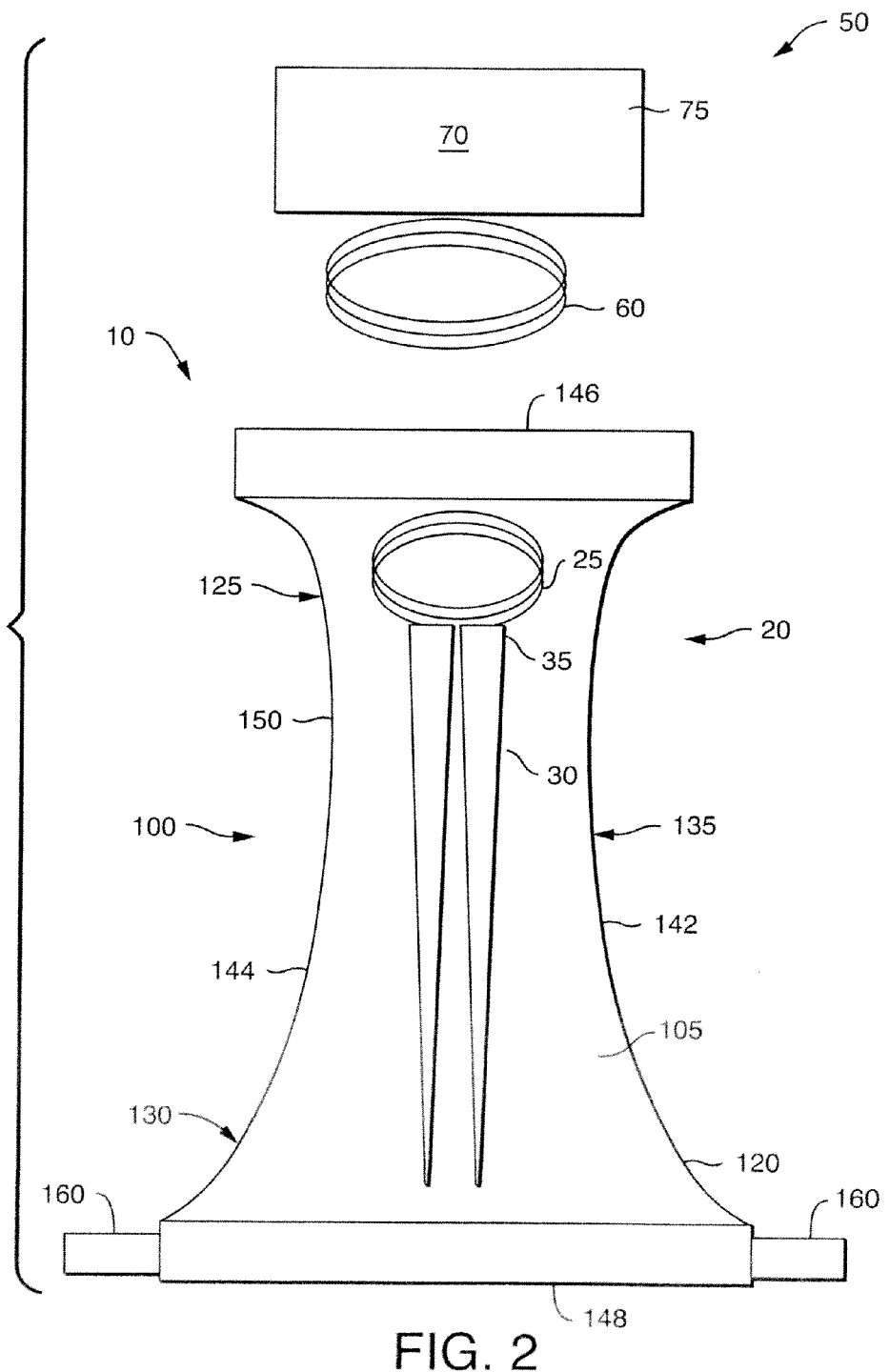
FIG. 2 is a schematic of the wetness sensor system of FIG. 1 as applied to a garment-type absorbent article.
Figure 3:
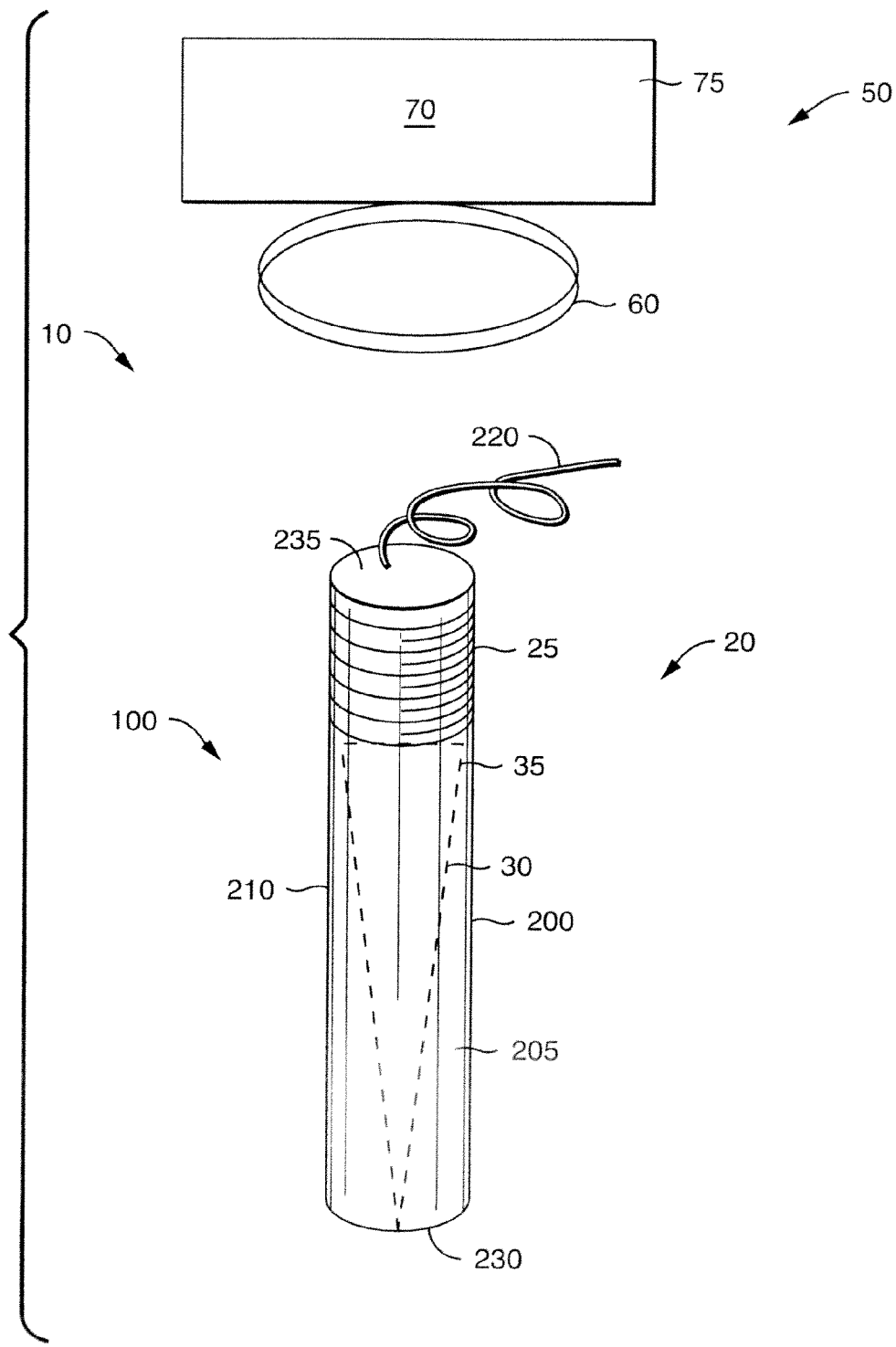
FIG. 3 is a schematic of the wetness sensor system of FIG. 1 as applied to a tampon.

The detector circuit 50 of the wetness detector system 10 includes an exciter coil 60 and sensor electronics 70. The exciter coil 60 is part of the detector circuit 50 as shown in FIGS. 1-3. Changes in the disposable absorbent article 100 are measured using the sensor coil 25 that is excited using the exciter coil 60, without any direct electrical connection between them.

The sensor electronics 70 also include a marginal oscillator circuit 75. The marginal oscillator circuit 75 is used to detect the altered impedance of the sensor coil 25. The marginal oscillator circuit 75, in its simplest form, is a standard Colpitts-type oscillator that has just barely enough feedback to drive it into oscillation. In other aspects of the present application, the marginal oscillator circuit 75 can be any suitable oscillator circuit including a Franklin or a Hartley oscillator, or a high precision impedance analyzer integrated circuit chip (e.g., AD7745 Analog Devices). When conductive objects are brought close to the sensor coil 25, energy is removed from the marginal oscillator circuit 75 due to ohmic losses in the conductive object. This removal of energy registers in the output of the marginal oscillator circuit 75, which in this case can be interpreted to measure either the amount of conductive liquid in the absorbent article 100 or the liquid's conductivity. Once the device is activated, the processor in the sensor electronics 70 takes a baseline measurement, which is automatic and transparent to the user. Once the wetness sensing system 10 is employed by a user, the sensor electronics 70 automatically zeroes itself to establish the point of zero wetness baseline needed.

The detector circuit 50 located outside the absorbent article 100 can be in the form of a clip-on-type device or a device that can be activated from outside as needed to monitor the status of the article in private or without disturbing the user. A signal detection algorithm is implemented such that the effects of orientation or angle of exciter coil 60 has minimal or no impact. The same remote monitor can be used to interrogate many absorbent articles in, for example, an institutional setting (i.e., no need to have one reader unit per article).

The wetness detector system 10 measures a physical property of the absorbent article 100 by measuring the changes in electrical properties of the exciter coils 60. Unlike previous induction coil wetness sensors such as those disclosed in U.S Patent Application Publication No. US2009/0124990 A1 (the '990 publication), the wetness detector system 10 of the present application uses two mutually-coupled planar and flexible coils 25, 60 to detect the wetness and/or time-to-change status of the article. The sensing coil in the '990 publication is disposed in the vicinity of the insult zone, the area of the disposable absorbent article in which an insult is expected. Practical implementation of such a sensing device for absorbent articles of smaller size is difficult due to the sizes of the electronics and of the sensing coil, and the power requirements of the device.

The present application overcomes these difficulties. Because the passive sensor coil 25 is inductively coupled, there is no need for a power source or an electronic circuit at the sensing location.

Because the exciter coil 60 is part of a marginal oscillator circuit 75, any change in the capacitance of the electrical double-layer capacitor 30 and the associated sensing coil 25 changes the output signal. The status of the absorbent article 100 can be monitored by measuring the changes in amplitude or frequency or phase. This change directly correlates with the status of the absorbent core and hence its saturation level. The detector circuit 50 outside of the disposable absorbent article 100 monitors the status of the interior of the disposable absorbent article 100 without touching that interior. This aspect enables absorbent article status monitoring without any process modifications or alterations. For example, only a flexographic printing of conducting patterns on the outer cover is needed in this case. The wetness sensors disclosed in U.S. Patent Application Publication No. 2010/0219841 A1 and in the '990 publication are based on changes in conductivity sensed by a single coil.

In the present application, the exciter coil 60 monitors changes in impedance in response to body waste in the proximity of the sensing coil 25, which is integrated within the sensor circuit 35. Due to the higher dielectric permittivity and conductivity of body waste relative to air, the initial impedance drastically changes when body waste is in the near-field of the sensor coil 25. When the sensor coil 25 is excited using a resonant circuit, the field penetrates into the absorber in the vicinity of the sensing coil 25.

One of the major challenges in such a sensor is to implement the technology in absorbent products such as a tampon. It is difficult to implement a wetness sensor in such products due to the size as well as space requirements. Also, wetness detection based on resistivity changes of conducting strips requires physical connection between the electronics and the conducting strips. The technology described herein overcomes that problem as there is no physical connection needed between the electronic circuit and the sensors to monitor the status of the article.

In one aspect of the present application, the detector circuit 50 can be disposed within a housing that protects the electronics and the user. The housing can be adapted to be attached to the absorbent article 100, or held in the vicinity of the absorbent article 100. If the housing is to be attached to the absorbent article 100 using an attachment mechanism, the housing can be a pouch or a rigid or semi-rigid housing that attaches to the outer cover 105, 205 of the absorbent article 100 near the region where insults are expected. Such attachment mechanism can use adhesive, hook and loop, mechanical fasteners such as snaps, a clip, or a clasp, any other suitable attachment mechanism, or any combination of these. Various attachment mechanisms include those disclosed in co-pending and co-assigned U.S. Patent Application Publication No. 2007/0142797 to Long, et al. and entitled "Garments With Easy-To-Use Signaling Device"; U.S. Patent Application Publication No. 2006/0244614 to Long and entitled "Connection Mechanisms"; and U.S. Patent Application Publication No. 2007/0024457 to Long, et al. and entitled "Connection Mechanisms In Absorbent Articles For Body Fluid Signaling Devices," which are incorporated herein by reference to the extent they are consistent (i.e., not in conflict) herewith.

The housing can also include electronics used to indicate product wetness or fullness caused by an insult. The electronics can emit an audible signal or a visual signal to indicate to the user that a body exudate is present in the absorbent article 100. The audible signal, for instance, can be as simple as one or more beeps or can emit a musical tune. Similarly, if the electronics issue a visible signal, the visible signal can include one light, multiple lights, or an interactive display. In still another aspect of the present disclosure, a receiver associated with the electronics can be configured to vibrate when the electronics are activated. The changes in impedance due to any insult can be indicated as a visual signal, an audio signal, or vibratory signal, or a combination of these. Such signals can alert the caregiver and/or user about the number of insults that have occurred and provide information about saturation level, so that the caregiver and/or user knows when the absorbent article should be changed. Light, audio, and/or vibration output signals can be successfully employed as alert mechanisms in absorbent articles. These alert circuits can be easily attached to a product or can be remotely activated by a radio frequency (RF) signal on a smart phone, indicator unit, at a remote location, or on any suitable device.

In an aspect of the present application, the detector circuit 50 is adapted to be held near the outermost surface of the outer cover 105, 205 of the absorbent article 100. In this aspect, no attachment mechanism is needed. The wearer of the absorbent article 100 or a caregiver holds the detector circuit 50 near the outer cover 105, 205 of the absorbent article 100 to detect whether the absorbent article 100 has received an insult. The detector circuit 50 can be associated with a cell phone, held in a pocket or purse, or otherwise kept in the vicinity of the sensor coil 25 such that the sensor coil 25 is able to communicate with the off-article components 50 when needed.

In some instances, it is conceivable that the wetness sensing system 10 needs to contend with nearby conductive objects that can cause interference. In practical applications, however, such a situation is unlikely because the interference-causing conductive object typically needs to be within one coil diameter of the coil's center. This makes the appearance of an interference-causing conductive object unlikely within one coil diameter of the center of the sensor coil 25 when the wetness sensing system 10 is used in conjunction with an absorbent article 100. Nevertheless, an interference problem of this sort can be managed by an intelligent processor that recognizes and stores signal output once the sensor coil 25 is in position and activated. The processor uses this signal output as a reference point and interprets subsequent signals in relation to this reference point. In other words, the processor includes an intelligent zeroing feature using specific modulation schemes to communicate between the sensor and exciter coils 25, 60. A higher sensitivity can be achieved if the natural resonant frequency of the passive sensor coil 25 is close to that of the exciter coil 60.

The present disclosure is directed to a wetness sensing system 10 used in conjunction with a disposable absorbent article 100. When the absorbent article 100 is insulted with a liquid, such as urine, menses, blood, or the like, the absorbent structure captures and retains the liquid. Conventional absorbent articles 100 are so effective at retaining liquid that caregivers might not know when an absorbent article 100 has been insulted. With traditional products the caregiver does not have any way of determining whether the absorbent article 100 has been insulted, especially with younger wearers of the absorbent article 100 because insults from younger wearers tend to be quite small.

Referring to FIGS. 2 and 3 for exemplary purposes, an absorbent article 100 that can be made in accordance with the present disclosure is shown. The absorbent article 100 might or might not be disposable. It is understood that the present disclosure is suitable for use with various absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

A generic garment-type absorbent article 120 is representatively illustrated in FIG. 2. The garment-type absorbent article 120 defines a pair of longitudinal end regions, otherwise referred to herein as a front region 125 and a back region 130, and a center region, otherwise referred to herein as a crotch region 135, extending longitudinally between and interconnecting the front and back regions 125, 130. The garment-type absorbent article 120 also defines an inner surface adapted in use (e.g., positioned relative to the other components of the article) to be disposed toward the wearer, and an outer surface opposite the inner surface. The front and back regions 125, 130 are those portions of the garment-type absorbent article 120 that, when worn, wholly or partially cover or encircle the waist or mid-lower torso of the wearer. The crotch region 135 generally is that portion of the garment-type absorbent article 120 that, when worn, is positioned between the legs of the wearer and covers the lower torso and crotch of the wearer. The garment-type absorbent article 120 has a pair of laterally opposite side edges 142, 144 and a pair of longitudinally opposite waist edges, respectively designated front waist edge 146 and back waist edge 148.

The illustrated garment-type absorbent article 120 includes a chassis 150 that, in this aspect, encompasses the front region 125, the back region 130, and the crotch region 135.

The chassis 150 includes an outer cover 105 and a bodyside liner (not shown) that can be joined to the outer cover 105 in a superimposed relation therewith and an absorbent structure (not shown) disposed between the outer cover 105 and the bodyside liner for absorbing liquid body exudates from the wearer. The chassis 150 can further include a pair of containment flaps (not shown) secured to the bodyside liner for inhibiting the lateral flow of body exudates.

The elasticized containment flaps define a partially unattached edge that assumes an upright configuration in at least the crotch region 135 of the garment-type absorbent article 120 to form a seal against the wearer's body. The containment flaps can extend longitudinally along the entire length of the chassis 150 or can extend only partially along the length of the chassis 150. Suitable constructions and arrangements for the containment flaps are generally well known to those skilled in the art.

To further enhance containment and/or absorption of body exudates, the garment-type absorbent article 120 can also suitably include leg elastic members (not shown), as are known to those skilled in the art. The leg elastic members can be operatively joined to the outer cover 105 and/or the bodyside liner and positioned in the crotch region 135 of the garment-type absorbent article 120. The leg elastic members can be formed of any suitable elastic material.

In some aspects, the garment-type absorbent article 120 can further include a surge management layer (not shown) that can be optionally located adjacent the absorbent structure and attached to various components in the garment-type absorbent article 120, such as the absorbent structure or the bodyside liner, by methods known in the art, such as by using an adhesive. A surge management layer helps to decelerate and diffuse surges or gushes of liquid that can be rapidly introduced into the absorbent structure of the garment-type absorbent article 120. Desirably, the surge management layer can rapidly accept and temporarily hold the liquid prior to releasing the liquid into the storage or retention portions of the absorbent structure.

The garment-type absorbent article 120 can further include a pair of opposing elastic side panels (not shown) that are attached to the back region 130 of the chassis 150. The side panels can be stretched around the waist and/or hips of a wearer to secure the garment-type absorbent article 120 in place. The side panels can be attached or bonded to the chassis 150 using any suitable bonding technique. In an alternative aspect, the elastic side panels can also be integrally formed with the chassis 150. For instance, the side panels can be an extension of the bodyside liner, of the outer cover 105, or of both the bodyside liner and the outer cover 105. The elastic side panels each have a longitudinal outer edge, a leg end edge disposed toward the longitudinal center of the training pant, and waist edges 146, 148 disposed toward a longitudinal end of the garment-type absorbent article 120.

The front and back regions 125, 130 of the garment-type absorbent article 120 can be connected by a fastening system 160 to define a three-dimensional configuration having a waist opening and a pair of leg openings. The waist opening of the garment-type absorbent article 120 is defined by the waist edges 146, 148 and encircles the waist of the wearer.

The side panels, if present, can be releasably attachable to the front region 125 of the article by the fastening system 160. It should be understood, however, that in other aspects, the side panels can be permanently joined to the chassis 150 at each end. The side panels can be permanently bonded together, for instance, when forming a training pant or absorbent swimwear.

The fastening system 160 can include laterally opposite first fastening components (not shown) adapted for refastenable engagement to corresponding second fastening components. The fastening components can be any refastenable fasteners suitable for absorbent articles.

The garment-type absorbent article 120 can include various waist elastic members (not shown) for providing elasticity around the waist opening. For example, the garment-type absorbent article 120 can include a front waist elastic member and/or a back waist elastic member.

The materials used to form the garment-type absorbent article 120 that surround the waist elastic members can vary depending upon the particular application and the particular product being produced.

The outer cover 105, for instance, can be breathable and/or can be liquid impermeable. The outer cover 105 can be constructed of a single layer, multiple layers, laminates, spunbond fabrics, films, meltblown fabrics, elastic netting, microporous webs, bonded-carded webs or foams provided by elastomeric or polymeric materials. The outer cover 105, for instance, can be a single layer of a liquid impermeable material, or alternatively can be a multi-layered laminate structure in which at least one of the layers is liquid impermeable. In other aspects, however, it should be understood that the outer cover 105 can be liquid permeable. In this aspect, for instance, the garment-type absorbent article 120 can contain an interior liquid barrier layer.

The inner layer of the outer cover 105 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover when a single layer, prevents waste material from wetting articles, such as bed sheets and clothing, as well as the wearer and caregiver.

The bodyside liner is suitably compliant, soft-feeling, and non-irritating to the wearer's skin. The bodyside liner is also sufficiently liquid permeable to permit liquid body exudates to readily penetrate through its thickness to the absorbent structure.

The absorbent structure can be disposed between the outer cover 105 and the bodyside liner. The absorbent structure can be any structure or combination of components that are generally compressible, conformable, non-irritating to a wearer's skin, and capable of absorbing and retaining liquids and certain body wastes. As a general rule, superabsorbent material is present in the absorbent web in an amount of from about 0 to about 90 weight percent based on total weight of the web. Superabsorbent materials are well known in the art.

After being formed or cut into a desired shape, the absorbent web material can be wrapped or encompassed by a suitable tissue or meltblown web or the like wrap sheet that aids in maintaining the integrity and shape of the absorbent structure. The absorbent web material can also be a coform material.

In various aspects of the present disclosure, the garment-type absorbent article 120 can include additional features such as those disclosed in co-pending and co-assigned U.S. patent application Ser. No. 11/303,283 to Long, et al. and entitled "Garments With Easy-To-Use Signaling Device";

and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the garment-type absorbent article 120 can also include other wetness sensing features such as fading ink, appearing ink, a wetness liner, or a cooling component.

In a similar manner illustrated in FIG. 3, the present disclosure can be applied to a tampon 200 as well. A tampon 200 is an absorbent article designed to be worn by a woman during her menstrual period to absorb menses and other body fluids. The tampon 200 includes an absorbent assembly (not shown) in the form of a tampon body 210 and also includes a withdrawal string 220. The tampon body 210 is normally compressed into the form of a cylinder and can have a blunt, rounded or shaped forward or distal end 230 that is closer to the cervix when the tampon 200 is in use. The tampon body 210 also has a proximal or string end 235 that is closer to the vaginal opening when the tampon 200 is in use. The withdrawal string 220 is fastened to the tampon body 210 and typically extends from the proximal end 235. The withdrawal string 220 serves as a means for withdrawing the tampon 200 from the woman's vagina. Catamenial tampons 200 suitable for use in the present disclosure include an absorbent material as is known in the art. The distal end 230 of the tampon body 210 or the tampon body 210 itself can be formed into specific shapes such as various cup shapes to enhance contact with the cervix, anterior formix, posterior formix, lateral formices, vaginal epithelium areas, or conformance to other anatomical areas within the vaginal or other cavity.

Tampons 200 can also leak, unbeknownst to the wearer, causing undesirable effects. Reasons for this leakage can include the shape of the tampon body 210 or the string 220 that, being absorbent, also can draw fluid out of the tampon body 210 causing leakage.

The tampon body 210 has an outer surface 205. The outer surface 205, the distal end 230, and the proximal end 235 together make up the perimeter of the tampon body 210.

A wetness detection system 10 can be used in conjunction with a tampon 200. The specific placement of the sensing coil 25 can be in a variety of places, including but not limited to the tampon string 220 or the proximal end 235 of the tampon body 210. Positioning the sensing coil 25 at the proximal end 235 of the tampon body 210, for example, would alert the wearer to wetness in the tampon 200 and to the possibility that leakage can occur.

Figure 4A:
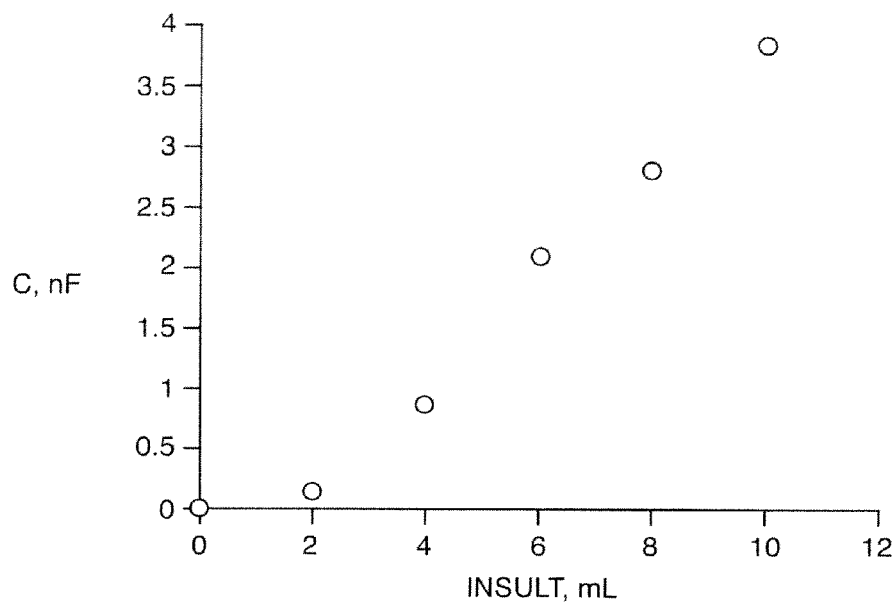
FIG. 4(*a*) illustrates the change in capacitance for different insults to a tampon of FIG. 3.
Figure 4B:
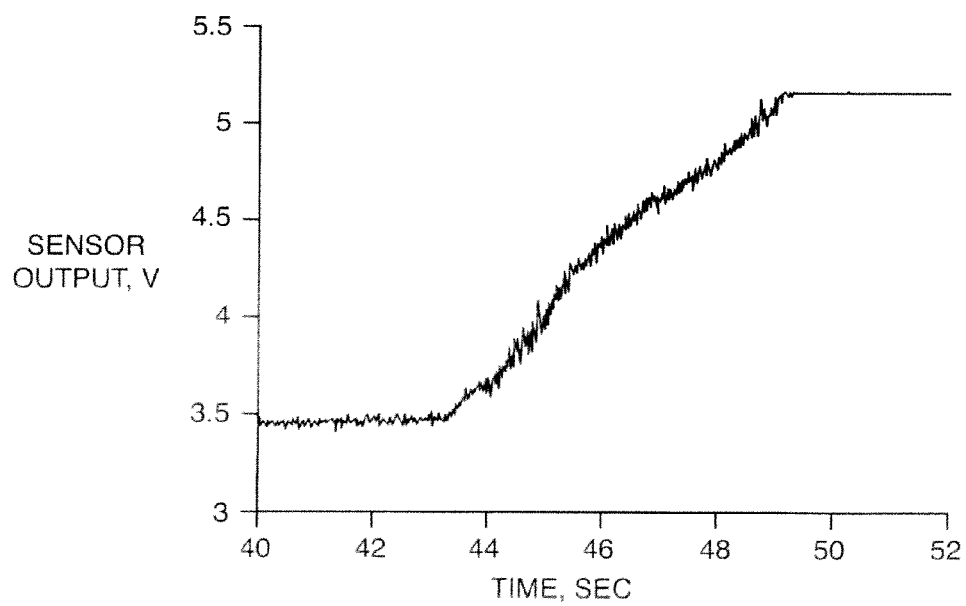

Schematic diagrams of the arrangement of contactless passive sensors on absorbent articles are presented in FIGS. 2 and 3. The electrical double-layer capacitor 30 can be printed inside the absorbent article 100 or it can be rolled as one of the layers to avoid any physical contact with the human body. A higher sensitivity is achieved due to the shape of the electrode as well as tuning of the resonant frequencies of the exciter and sensor coils 60, 25. Various electrode shapes can be incorporated into this design, depending on the absorbent article 100. Bench tests are conducted using a 0.9% saline solution. FIG. 4(a) shows the measured change in capacitance due to a 10 ml insult on a tampon 200. The change in capacitance is measured using a capacitance meter. FIG. 4(b) presents the change in output DC voltage measured from the marginal oscillator due to a 10 ml insult on a tampon 200. The amplitude of the oscillator signal changes due to the changes in the electrical double-layer capacitor 30. The change in amplitudes due to the insult on an absorbent article 100 is presented in FIGS. 5 and 6.

Figure 5:
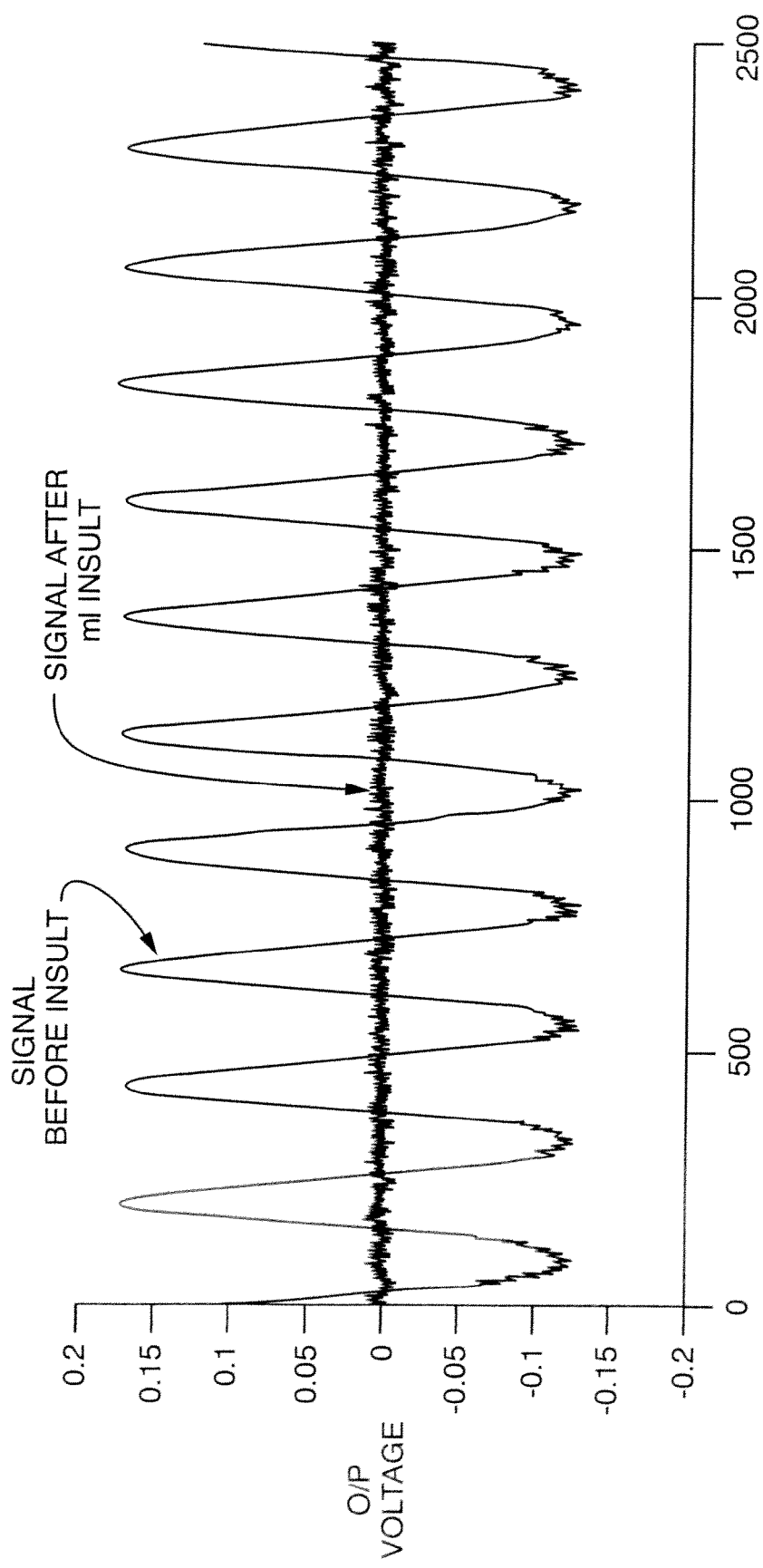
FIG. 5 illustrates the measured change in signal characteristics due to a 10 ml saline insult to a step 1 diaper such as that of FIG. 2, with an electrical double-layer capacitor disposed on the inside surface of the outer cover.
Figure 6:
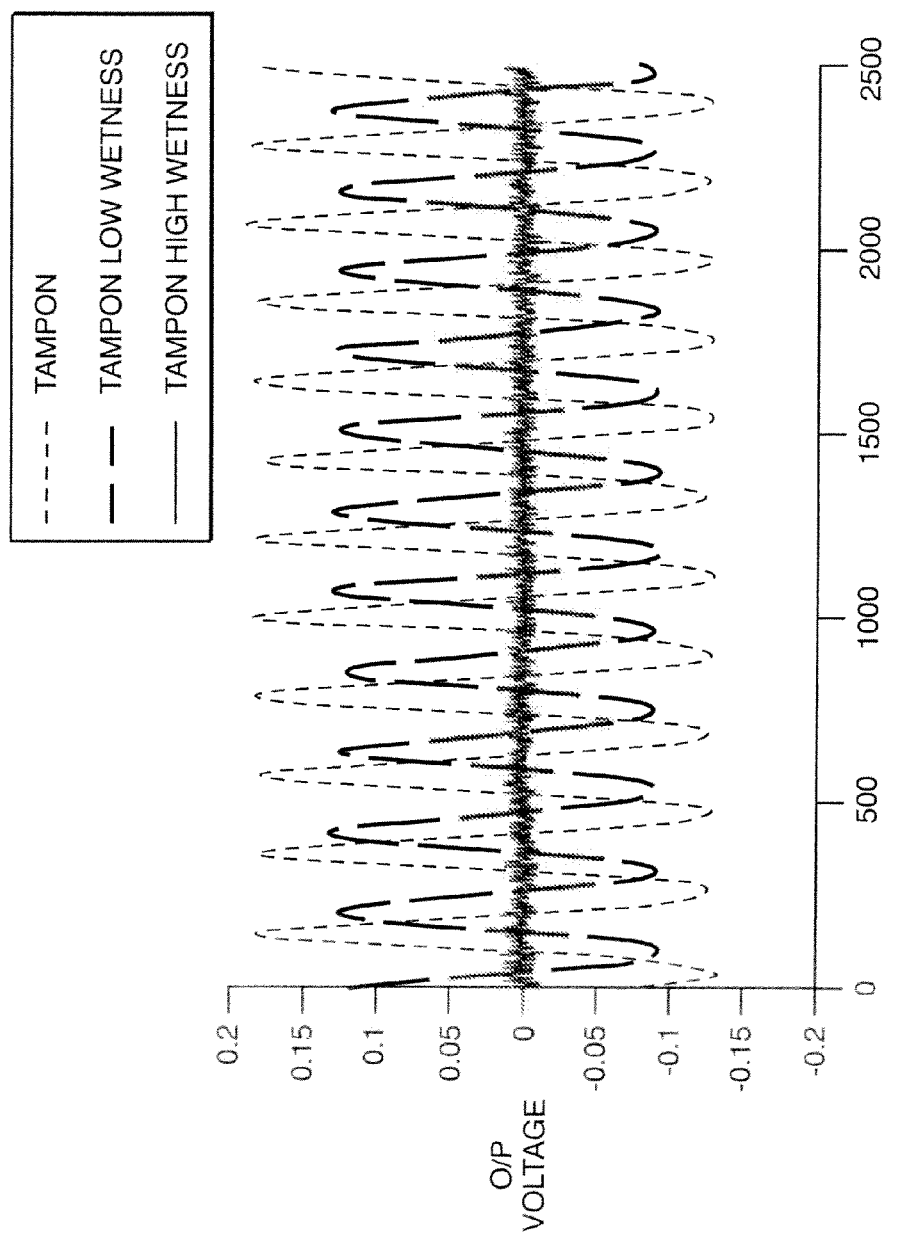
FIG. 6 illustrates the change in signal characteristics due to various insults to a tampon such as that of FIG. 3.

FIG. 5 shows the measured signal change due to a 10 ml insult on a step 1 diaper with the electrical double-layer capacitor 30 on the inside of the outer cover 105. FIG. 6 presents the measured signal change from a tampon 200 for different wetness level with the sensor coil 25 wound as shown in FIG. 3.

These and other modifications and variations to the present disclosure can be practiced by those of ordinary skill in the art, without departing from the spirit and scope of the present disclosure, which is more particularly set forth in the appended claims. In addition, it should be understood that aspects of the various aspects can be interchanged both in whole and in part. Furthermore, those of ordinary skill in the art will appreciate that the foregoing description is by way of example only, and is not intended to limit the disclosure so further described in such appended claims.

What is claimed is:

1. An absorbent article facilitating sensing the presence of a body exudate in the absorbent article, the article comprising:
   an absorbent member;
   a sensor coil disposed on or in the article; and
   an electrical double-layer capacitor disposed on or in the article and in electrical communication with the sensor coil, wherein the capacitor is in fluid communication with the absorbent member.

2. The article of claim 1, wherein the electrical double-layer capacitor includes a pair of plates each having a proximal end adjacent the sensor coil and a distal end spaced apart from the sensor coil.

3. The article of claim 2, wherein the plates taper in width from the proximal end to the distal end.

4. The article of claim 3, wherein at least one plate includes conductive paper.

5. The article of claim 4, wherein the conductive paper includes conductive fibers with a total surface area of at least 5 square meters per gram of conductive paper.

6. The article of claim 4, wherein the conductive paper includes conductive fibers with a total surface area of at least 100 square meters per gram of conductive paper.

7. The article of claim 1, wherein the electrical double-layer capacitor is configured to receive an excitation voltage from the sensor coil, and wherein the excitation voltage is less than 100 mv.

8. The article of claim 1, wherein the electrical double-layer capacitor is configured to receive an excitation voltage from the sensor coil, and wherein the excitation voltage is less than 50 mv.

9. The article of claim 1, wherein the electrical double-layer capacitor is configured to receive an excitation voltage from the sensor coil, and wherein the excitation voltage is less than 10 mv.

10. The article of claim 1, wherein the article includes an outer surface, and wherein the sensor coil is disposed on the outer surface.

11. The article of claim 10, wherein the sensor coil is printed on the outer surface.

12. The article of claim 1, wherein the article includes a cover sheet having an inner surface and an outer surface, and wherein the sensor coil is disposed on the inner surface.

13. The article of claim 12, wherein the sensor coil is printed on the inner surface.

14. An absorbent article system for sensing and indicating the presence of a body exudate in an absorbent article, the system comprising:
   an absorbent article including
      an absorbent member, a sensor coil disposed on or in the article, and
an electrical double-layer capacitor disposed on or in the article and in electrical communication with the sensor coil, wherein the capacitor is in fluid communication with the absorbent member; and
a detector circuit including
an exciter coil configured for electromagnetic communication with the sensor coil, and
sensor electronics configured to indicate the presence of a body exudate based on changes in the electromagnetic communication between the exciter coil and the sensor coil.

15. The system of claim 14, wherein the detector circuit is disposed within a housing.

16. The system of claim 14, wherein the electrical double-layer capacitor includes a pair of plates each having a proximal end adjacent the sensor coil and a distal end spaced apart from the sensor coil, wherein the plates taper in width from the proximal end to the distal end, and wherein at least one plate includes conductive paper.

17. The system of claim 14, wherein the article includes an outer surface, and wherein the sensor coil is disposed on the outer surface.

18. The system of claim 14, wherein the article includes a cover sheet having an inner surface and an outer surface, and wherein the sensor coil is disposed on the inner surface.

19. The system of claim 14, wherein the detector circuit is adapted to provide a wireless notification.

20. The system of claim 14, wherein the detector circuit is adapted to be held adjacent the absorbent article.

* * * * *